(12) United States Patent
Ono

(10) Patent No.: US 7,826,596 B2
(45) Date of Patent: Nov. 2, 2010

(54) RADIATION THERAPY APPARATUS

(75) Inventor: Tomukazu Ono, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/035,919

(22) Filed: Feb. 22, 2008

(65) Prior Publication Data
US 2008/0205597 A1 Aug. 28, 2008

(30) Foreign Application Priority Data
Feb. 27, 2007 (JP) ............... 2007-047656

(51) Int. Cl.
*G21K 1/04* (2006.01)
(52) U.S. Cl. .................. 378/152; 378/65; 378/153
(58) Field of Classification Search ............ 378/152, 378/153, 65
See application file for complete search history.

(56) References Cited
U.S. PATENT DOCUMENTS
6,814,489 B2 * 11/2004 Jensen et al. ............... 378/197

2005/0185766 A1 * 8/2005 Tsujita ....................... 378/150

FOREIGN PATENT DOCUMENTS
JP 07-067491 B * 7/1995
JP 2002-210026 7/2002

OTHER PUBLICATIONS
English language translation of JP07-067491B.*

* cited by examiner

*Primary Examiner*—Hoon Song
*Assistant Examiner*—Mona M Sanei
(74) *Attorney, Agent, or Firm*—Oblon, Spivak, McClelland, Maier & Neustadt, L.L.P.

(57) ABSTRACT

A radiation therapy apparatus has a multi-leaf collimator device having a pair of collimator components which respectively comprise a plurality of leaves arranged close to one another such that the leaves face one another across an irradiation axis, and configured to set a desired irradiation field by individually moving the leaves. One of the collimator components is arranged with an offset with respect to the other collimator component, within a range of a leaf-width.

8 Claims, 8 Drawing Sheets

RADIATION THERAPY APPARATUS

BACKGROUND OF THE INVENTION

1. Field of the Invention

The present invention relates to a radiation therapy apparatus used for a therapy of diseases such as malignant tumors, and particularly to the radiation therapy apparatus including a multi-leaf collimator device which allows an extent of an object that is exposed to radiation (which will be referred to as an "irradiation field" hereafter) to be set with high precision.

2. Description of the Related Art

From the perspective of radiation protection, the radiation therapy apparatus includes a collimator device formed of a material the nature of which renders it impermeable to radiation such as tungsten or the like, thereby allowing the exposure to radiation to be limited to a therapy part including a body. Such a collimator device needs to have a function of carefully forming the irradiation field that approximates a shape of the therapy part without a formation of a penumbra. Accordingly, such a collimator device has a first collimator and a second collimator arranged in the irradiation direction such that they overlap.

With such an arrangement, the first collimator provided on a near side of a radiation source is configured in a form of a single unit comprising a pair of members disposed such that they face each other across an irradiation axis. Such an arrangement allows that the members drive so as to adjust a distance therebetween. For example, the members drive along an arc-shaped path around the radiation source as a center. On the other hand, the second collimator provided on a far side of the radiation source is configured in the form of a pair of collimator components (blocks) such that the collimator components face each other across the irradiation axis in an orthogonal direction to a moving direction of the first collimator. Each of the collimator components of the second collimator has multiple leaves arranged close to one another, which can be individually moved so as to adjust a distance therebetween along the arc-shaped path around the radiation source as the center.

The second collimator is the so-called multi-leaf collimator device comprising a pair of collimator components 1A and 1B arranged symmetrically, as shown in FIG. 8, for example. The collimator component 1A has tens of leaves 1A1-1An arranged close to one another. The collimator component 1B has tens of leaves 1B1-1Bn arranged close to one another. The leaves 1A1-1An and the leaves 1B1-1Bn can be adjusted individually along the arc-shaped path. Such an arrangement allows these leaves to be driven individually along the arc-shaped pat by respective driving devices each of which is provided to the corresponding leaf. Such an arrangement allows the first collimator comprising the collimator components facing each other to be moved in an X direction so as to adjust the distance therebetween. In addition, such an arrangement allows the leaves 1A1-1An and the leaves 1B1-1Bn facing one another to be moved individually in a Y direction so as to adjust the distance therebetween. Such a combination of adjustment operations provides a formation of an irradiation field "U" in a desired shape that approximates the shape of the therapy part. Such an arrangement allows the leaves facing one another to be moved along the arc-shaped path, thereby providing irradiation without the formation of the penumbra in the irradiation field "U".

It is extremely important for the radiation therapy apparatus to irradiate only the therapy part which is approximately equal to a focus without exposing a healthy tissue to radiation. From this point of view, the multi-leaf collimator provides an extremely important function. However, the focus develops in various shapes. This leads to difficulty in providing the irradiation field "U" that matches the shape of such a focus. In order to solve this problem, examples of conceivable arrangements include an arrangement in which the collimator components 1A and 1B include the leaves 1A1-1An and 1B1-1Bn, respectively, which are a minute pitch. Such an arrangement requires as many leaves A1-1An and 1B1-1Bn as possible, by narrowing a leaf-width.

However, such an arrangement having an increased number of leaves, which provides the minute pitch, requires leaves with a reduced the leaf-width. Even with ordinary arrangements, the leaves are formed with the leaf-width of around 2 to 3 [mm]. An arrangement having leaves with a narrower width than those of ordinary leaves has problems in the manufacturing process due to warped leaves etc., examples of which include difficulty in manufacturing the collimator with a desired level of precision.

In addition, these leaves must be moved individually so as to provide the desired irradiation field. Such an arrangement requires respective driving device. This leads to difficulty in designing a layout of a supporting mechanism and a driving mechanism, which allow such a great number of leaves arranged closely adjacent to one another to be individually moved, and the layout of a detection mechanism for detecting a movement of each leaf. Furthermore, in order to prevent radiation leaks from gaps between the adjacent leaves, there is a need to arrange the leaves with as small the gap as possible between the adjacent leaves, e.g., with the gap of around 0.05 to 0.1 [mm]. However, it is extremely difficult to provide such high-precision manufacturing and fabrication in order to realize such a design.

In view of such a situation, an arrangement has been proposed in which the second collimator is provided in a form of two separate stages arranged with a predetermined interval along an irradiation direction. With such an arrangement, the leaves are arranged with an offset between an upper-stage collimator and a lower-stage collimator such that each boundary between the adjacent leaves including upper-stage collimator components respectively does not match any of the boundaries between the adjacent leaves of the lower-stage collimator components respectively (see "Japanese Patent Publication (Laid-open: KOKAI) No. 2002-210026", for example). With such an arrangement, although the leaves are formed with the same leaf-width as those of the ordinary arrangements, such an arrangement provides the same effect as that provided by an arrangement having leaves formed with half the leaf-width of those of the ordinary arrangements. This is able to make the irradiation field further minute. Such an arrangement allows the shape of the irradiation field to be adjusted with higher precision such that it approximates the therapy part, thereby protecting the healthy tissue from being exposed to radiation.

Such a technique disclosed in the aforementioned Japanese Patent publication can eliminate to a certain extent the problem of an arrangement having an increased number of leaves formed with a reduced leaf-width. However, such a technique provides an arrangement in which the second collimator is provided in the form of two separate stages arranged with an interval in the irradiation direction. Accordingly, the number of components required for the supporting mechanism and the driving mechanism, which allow the leaves to be individually moved, and the number of components required for the detection mechanism for detecting the movement of each leaf, are twice those of the ordinary arrangements. This leads to a complicated configuration and a larger-sized collimator device, which are new problems. Such a larger-sized collimator leads to reduction in a space for the therapy, which is a problem of the radiation therapy apparatus itself.

SUMMARY OF THE INVENTION

The present invention has been made in order to solve the aforementioned problems. Accordingly, it is an object thereof to provide the radiation therapy apparatus including the multi-leaf collimator device having a function of adjusting the irradiation field with high resolution such that it approximates the shape of the therapy part using the second collimator provided in the form of a single stage, i.e., not in the form of two stages, without increasing the number of leaves.

To solve the above-described problems, the present invention provides the radiation therapy apparatus, comprising: A radiation therapy apparatus comprising: a multi-leaf collimator device having a pair of collimator components which respectively comprise a plurality of leaves arranged close to one another such that the leaves face one another across an irradiation axis, and configured to set a desired irradiation field by individually moving the leaves, wherein one of the collimator components is arranged with an offset with respect to the other collimator component, within a range of a leaf-width.

To solve the above-described problems, the present invention provides the radiation therapy apparatus, comprising: a multi-leaf collimator device having a pair of collimator components which respectively comprise a plurality of leaves arranged close to one another such that the leaves face one another across an irradiation axis, and configured to set a desired irradiation field by individually moving the leaves, wherein at least one of the collimator components is configured such that it can be relatively moved with respect to the other collimator component, within a range of a leaf-width.

DESCRIPTION OF THE PREFERRED EMBODIMENTS

Figure 1:
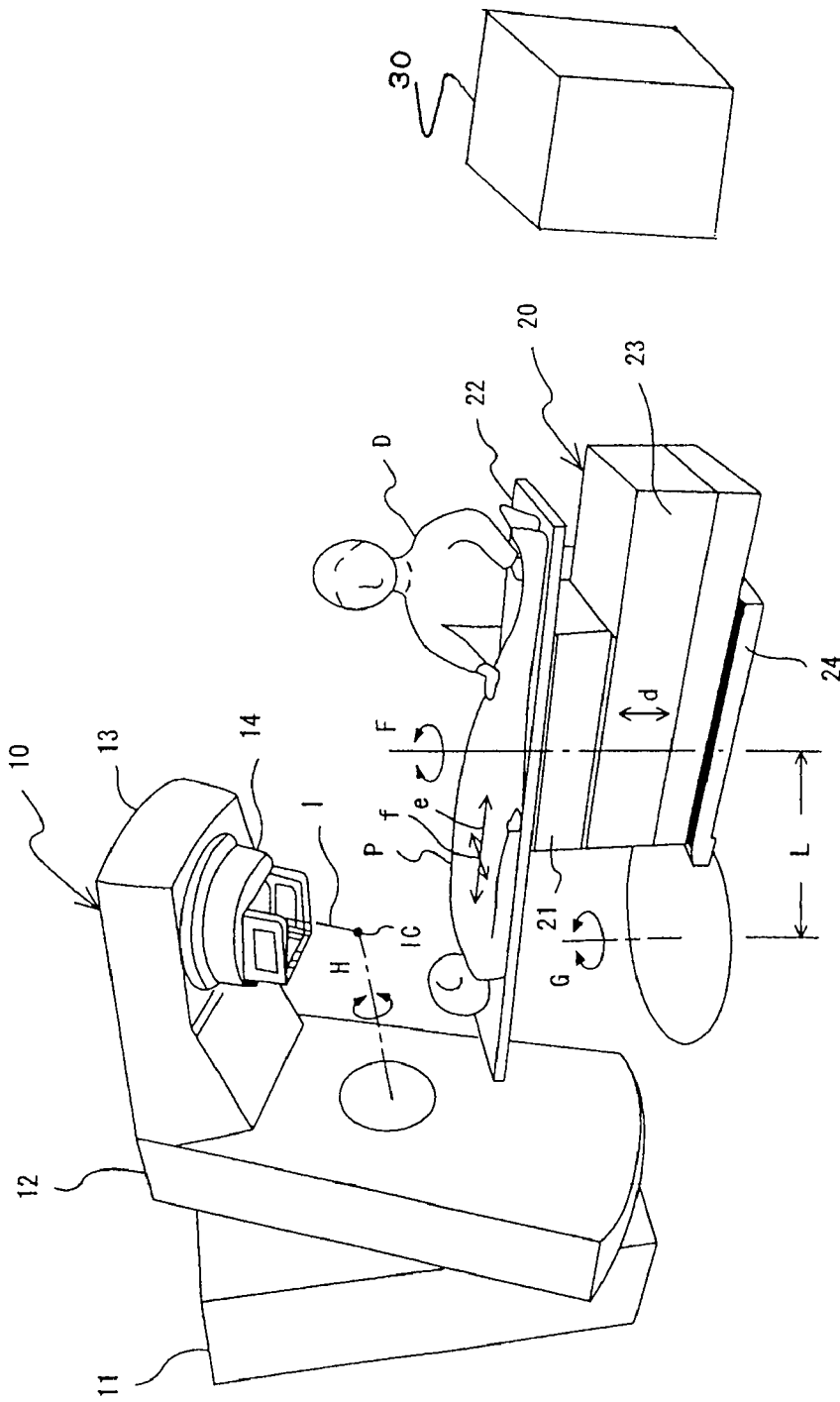
FIG. 1 is an external view which shows a usage condition of the radiation therapy apparatus according to a present embodiment.

Detailed description will be made with reference to FIG. 1 through FIG. 7 regarding a radiation therapy apparatus including a multi-leaf collimator device according to an embodiment of the present invention. It should be noted that, in these drawings, the same components are denoted by the same reference numerals.

FIG. 1 is an external view which shows a usage condition of the radiation therapy apparatus according to a present embodiment. First, description will be made in a schematic fashion with reference to FIG. 1 regarding a configuration of the radiation therapy apparatus according to the present embodiment.

In broad terms, the radiation therapy apparatus has an irradiation device 10 which uses a radiation source to irradiate a predetermined direction, a therapy table 20 on which an object (a person who needs a therapy) P, including a focus, lies and which sets a positioning of a therapy part to be irradiated, and a control device 30 which organically controls a components of the radiation therapy apparatus, e.g., the irradiation device 10 and the therapy table 20.

The irradiation device 10 includes a fixed frame 11 installed on a floor, a turnable frame 12 which is turnably supported by the fixed frame 11, an irradiation head 13 provided to a tip portion extending in the horizontal direction from one end of the turnable frame 12, and a collimator device 14 which is a built-in component of the irradiation head 13. With such an arrangement, the turnable frame 12 can be turned with respect to the fixed frame 11 over approximately 360 degrees around a rotation center axis "H" extending in the horizontal direction. Furthermore, the collimator device 14 is provided such that it can be turned with respect to the irradiation head 13 around an irradiation axis "I". It should be noted that the intersection of a rotation center axis "H" for the turnable frame 12 and the irradiation axis "I" will be referred to as the "isocenter (IC)" hereafter. With such an arrangement, the turnable frame 12 is configured such that it can be turned according to various kinds of irradiation, examples of which include a rotation irradiation, a pendulum irradiation, an intermittent irradiation, etc.

Furthermore, the therapy table 20 is installed on the floor such that it can be turned over a predetermined angle range in a direction of arrow "G" along an arc with the isocenter IC as a center. Furthermore, a table-top 22, on which the object P can lie, is provided to a top of the therapy table 20. Here, the table-top plate 22 is supported by an upper portion mechanism 21. The upper portion mechanism 21 includes a mechanism which allows the table-top 22 to be moved in a longitudinal direction indicated by an arrow "e" and a lateral direction indicated by an arrow "f".

Furthermore, the upper portion mechanism 21 is supported by an elevator mechanism 23. The elevator mechanism 23 has a link mechanism, for example. Such an arrangement allows the elevator mechanism 23 itself to be moved in a vertical direction indicated by an arrow "d", thereby allowing the upper portion mechanism 21 and the table-top 22 to be moved in a predetermined range in the vertical direction. Moreover, the elevator mechanism 23 is supported by a lower portion mechanism 24. The lower portion mechanism includes a mechanism which allows the elevator mechanism 23 to be turned in the direction indicated by an arrow "F", with the position that is distant from the isocenter IC by a distance "L" as the center. Such an arrangement allows the upper portion mechanism 21 and the table-top 22 to be turned in a predetermined range of angle in the direction indicated by the arrow "F", in addition to the elevator mechanism 23.

It should be noted that such an arrangement allows a medical staff "D" such as a surgeon or the like to operate an operation unit provided to the control device 30, thereby setting the positioning of the object P and adjusting the collimator device 14 which defines an irradiation field at a radiation therapy.

It is important for the radiation therapy to irradiate only the therapy part in a concentrated manner without damaging a normal tissue. The collimator device 14 controls a position to be irradiated, which protects the normal tissue from being exposed to radiation. With such an arrangement, the collimator device 14 is provided in the form of a built-in component of the irradiation head 13 such that it can be turned around the irradiation axis "I".

Figure 2:
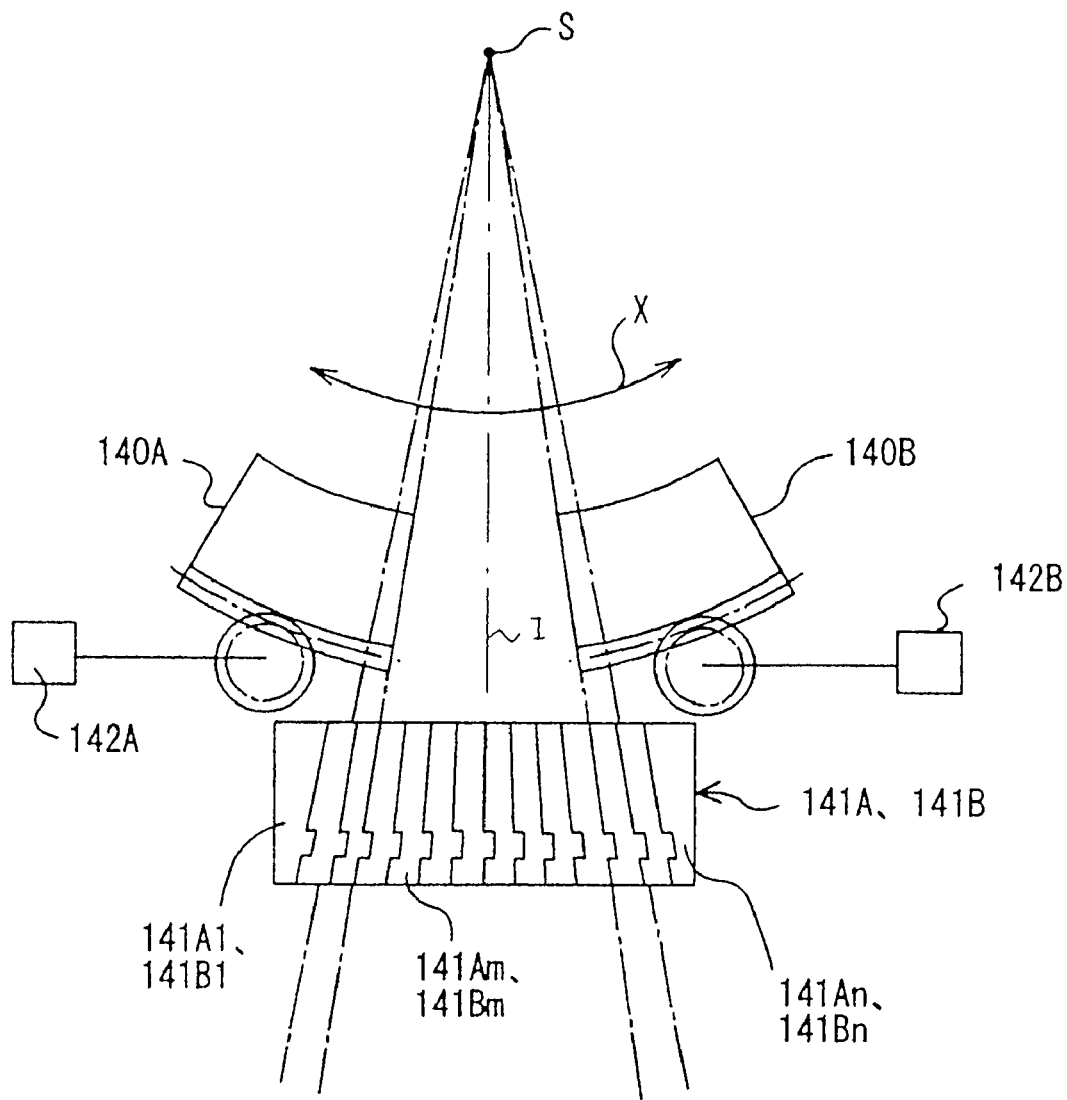
FIG. 2 is a side view which shows a driving direction of the first collimator included the collimator device in the present embodiment.
Figure 3:
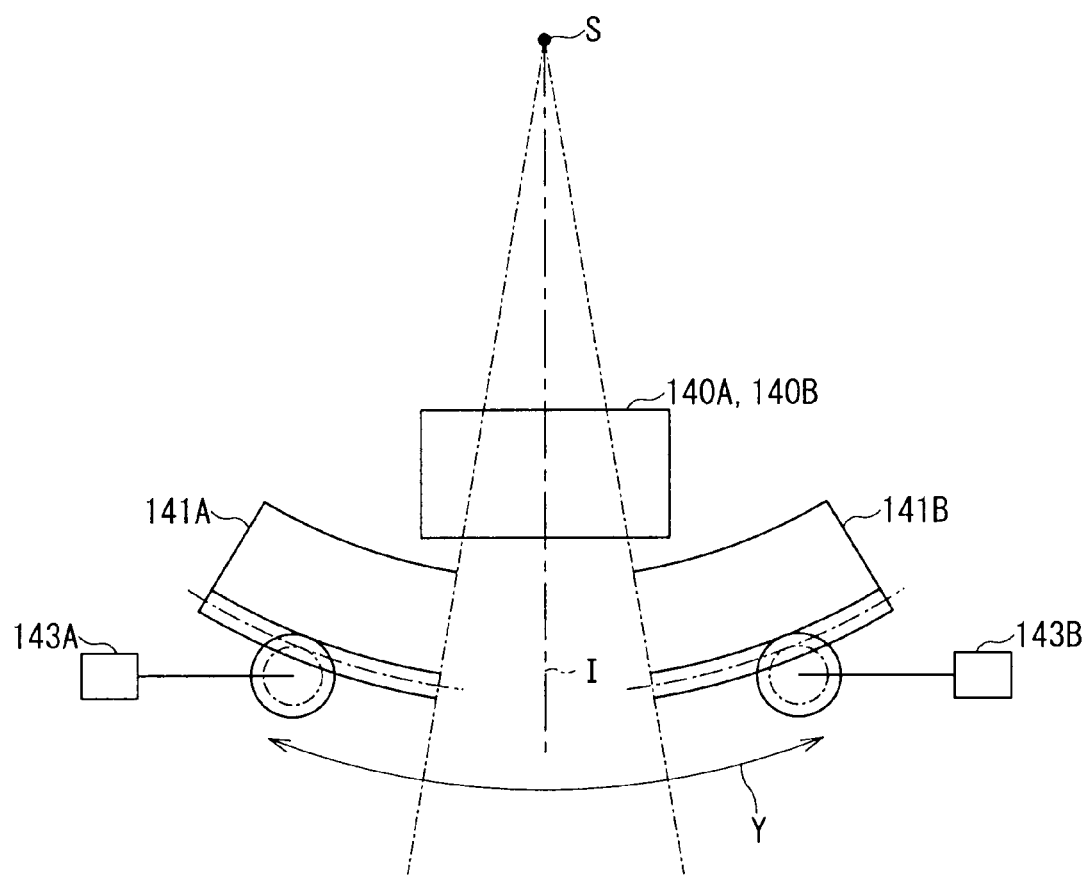
FIG. 3 is a side view which shows a first example of a driving direction of the second collimator provided to the collimator device in the present embodiment.
Figure 4:
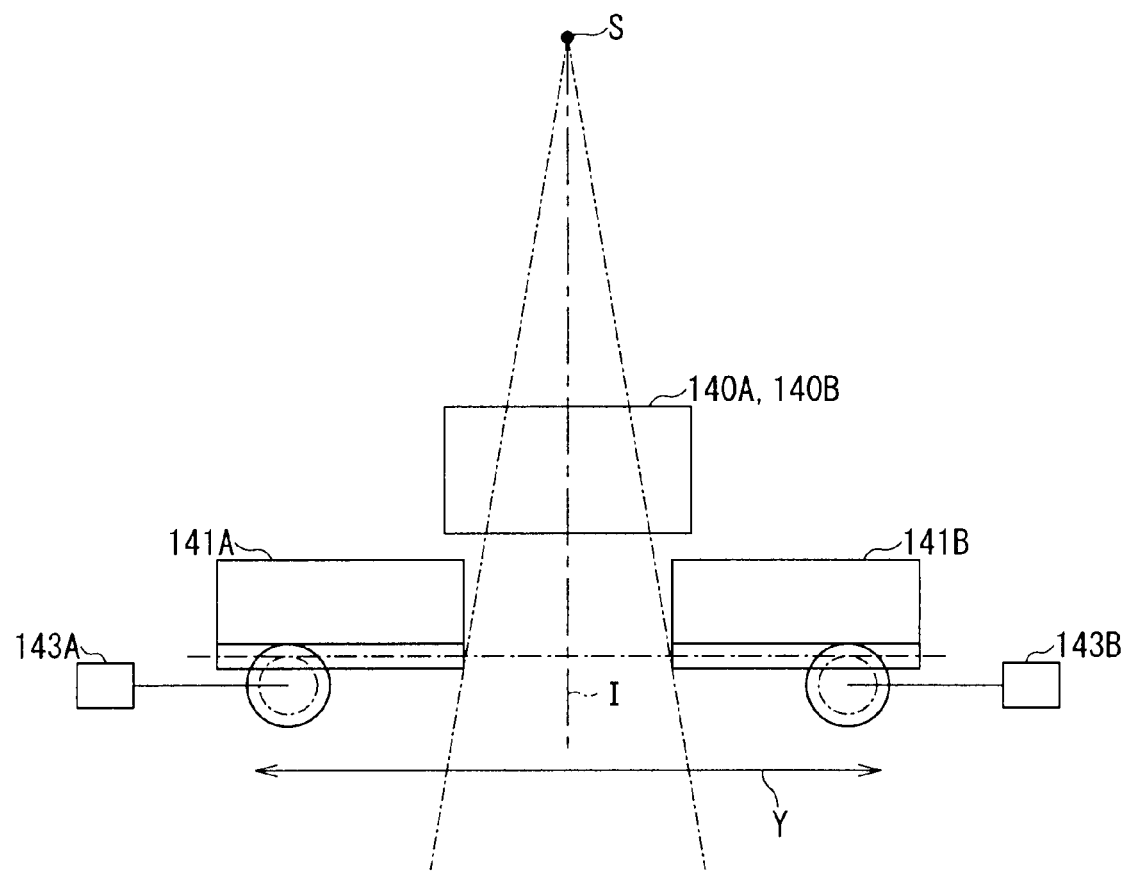
FIG. 4 is a side view which shows a second example of a driving direction of the second collimator provided to the collimator device in the present embodiment.
Figure 5:
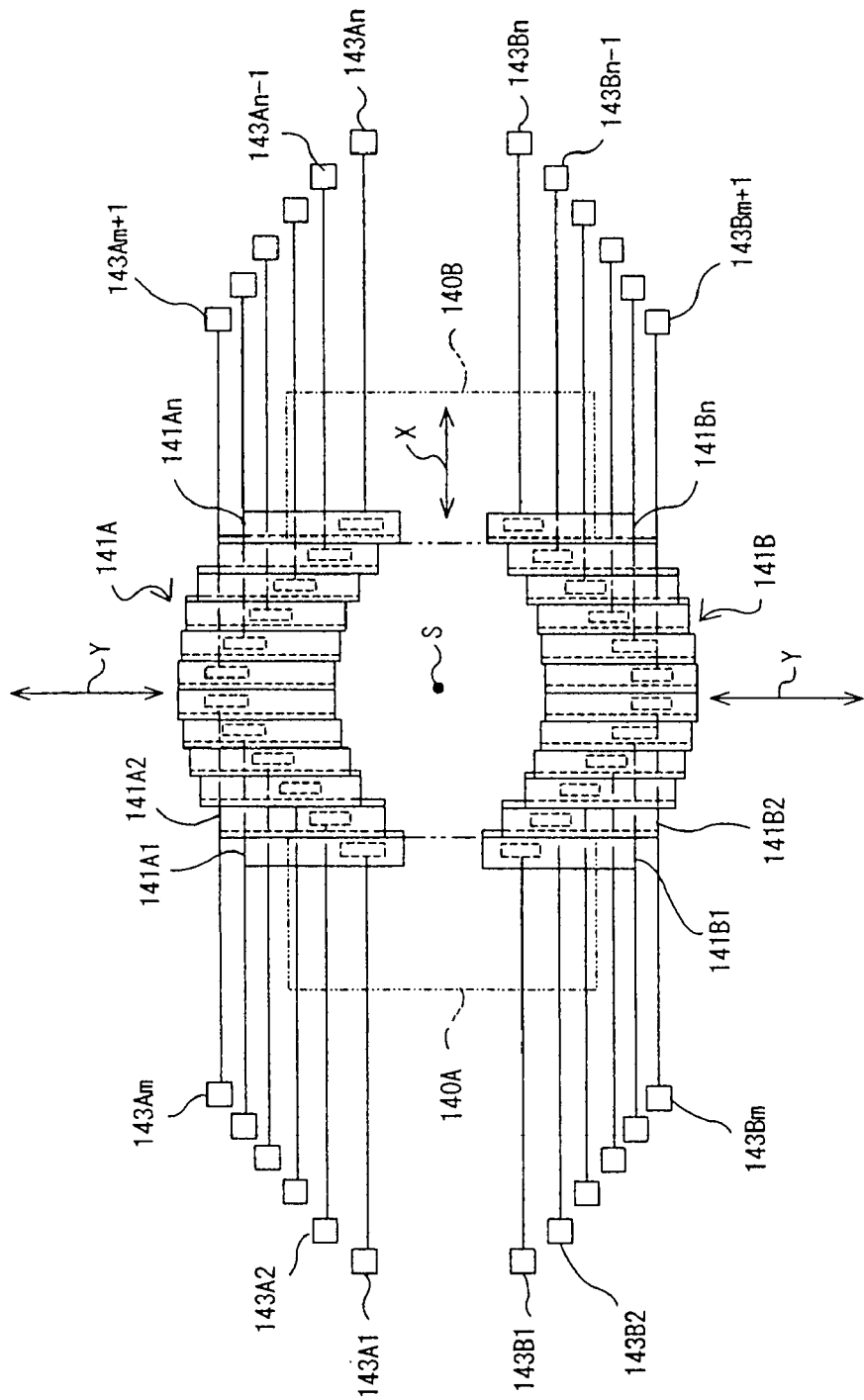
FIG. 5 is a top view which shows a constitution example of the second collimator provided to the collimator device in the present embodiment.
Figure 6:
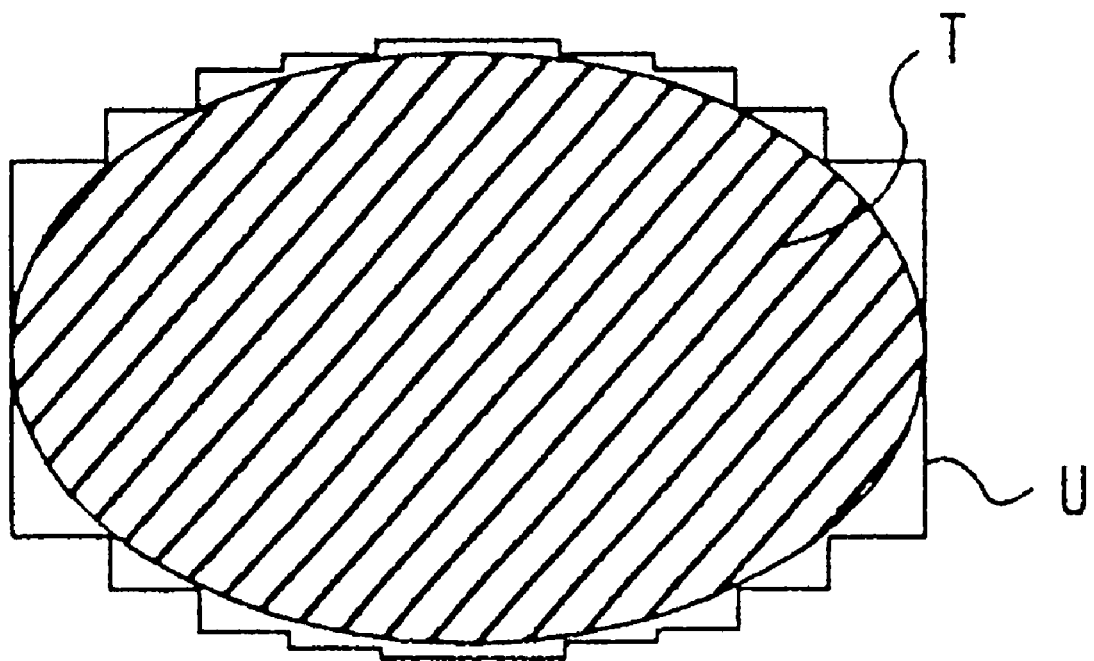
FIG. 6 is a top view which shows the irradiation field example of the second collimator in the present embodiment.

Next, description will be made regarding the collimator device 14 with reference to FIG. 2 through FIG. 7. FIG. 2 is a side view which shows the driving direction of the first collimator provided to the collimator device 14. FIG. 3 is a side view which shows a first example of a driving direction of the second collimator provided to the collimator device 14. FIG. 4 is a side view which shows a second example of a driving direction of the second collimator provided to the collimator device 14. It should be noted that FIG. 3 and FIG. 4 show the collimator device 14 viewed in an orthogonal direction orthogonal to the direction in which the collimator 14 shown in FIG. 2 is viewed. Furthermore, a housing of the collimator device 14 is not shown in these drawings. FIG. 5 is a top view which shows a constitution example of the second collimator provided to the collimator device 14 in the present embodiment.

As shown in FIG. 2 through FIG. 4, in general, the collimator device 14 has two kinds of collimators (a first collimator 140 and a second collimator 141) formed of a heavy metal such as tungsten or the like. These two kinds of collimators are arranged along the irradiation direction from the radiation source "S" such that they overlap. With such an arrangement, each of the collimators 140 and 141 has a pair of separate components arranged such that they face each other (see the components denoted by reference numerals 140A, 140B, 141A, and 141B in FIG. 2 and FIG. 3). Here, such a pair of components forming the collimator 140 or 141 is differentiated by reference symbols "A" and "B" for convenience of understanding.

With such an arrangement, each of the first collimator component 140A and the second collimator component 140B provided on a near side of the radiation source "S" is configured in the form of a single unit, as clearly shown in FIG. 2. Furthermore, the collimator components 140A and 140B are arranged such that an end face of the collimator component 140A and an end face of the collimator component 140B face each other across the irradiation axis "I". Such an arrangement allows the collimator elements 140A and 140B to be moved in a direction of an arrow "X" along an arc-shaped path around the radiation source "S" as a center by driving devices 142A and 142B, thereby adjusting a distance between the collimator components 140A and 140B.

Also, the second collimator components 141A and 141B provided on a far side of the radiation source "S" can be moved along the arc-shaped path, as clearly shown in FIG. 3. Furthermore, the collimator components 141A and 141B are arranged such that an end face of the collimator component 141A and an end face of the collimator component 141B face each other across the irradiation axis "I". Such an arrangement allows the collimator elements 141A and 141B to be moved by driving devices 143A and 143B in the orthogonal direction to the aforementioned arranging direction of the collimator elements 140A and 140B, i.e., in a direction of an arrow "Y" along the arc-shaped path around the radiation source "S" as the center, thereby adjusting a distance between the collimator components 141A and 141B.

In another example shown in FIG. 4, the second collimator components 141A and 141B are arranged such that the end face of the collimator component 141A and the end face of the collimator component 141B face each other across the irradiation axis "I". Such an arrangement allows the collimator elements 141A and 141B to be moved by the driving devices 143A and 143B in the orthogonal direction to an arranging direction of the first collimator elements 140A and 140B, i.e., in the direction of the arrow "Y" along a straight path, thereby adjusting the distance between the collimator components 141A and 141B.

Note that description will be made below regarding an arrangement which allows the first collimator 140 to be driven in the driving direction "X" as described with reference to FIG. 2, and which allows the second collimator 141 to be driven in the driving direction "Y" as described with reference to FIG. 3.

As shown in FIG. 2, the second collimator component 141A (141B) has multiple leaves 141A1-141An (141B1-141Bn) arranged close to one another. FIG. 5 shows the detailed configuration thereof.

That is to say, driving devices 143A1-143An (143B1-143Bn) are provided to the respective leaves 141A1-141An (141B1-141Bn) forming the second collimator component 141A (141B). Such an arrangement allows the leaves 141A1-141n (141B1-141Bn) to be driven individually in the direction of the arrow "Y" along the arc-shaped path around the radiation source "S" as the center, thereby adjusting the distances therebetween.

Such an arrangement allows the leaves 141A1-141An of the second collimator component 141A and the leaves 141B1-141Bn of the second collimator component 141B to be moved individually in the "Y" direction so as to adjust the distance therebetween, in addition to allowing the first collimator components 140A and 140B to be moved in the "X" direction so as to adjust the distance therebetween. The combination of these operations allows the irradiation field "U" to be formed in a desired shape such that it approximates the shape of the therapy part "T" which is approximately equal to the focus.

Figure 8:
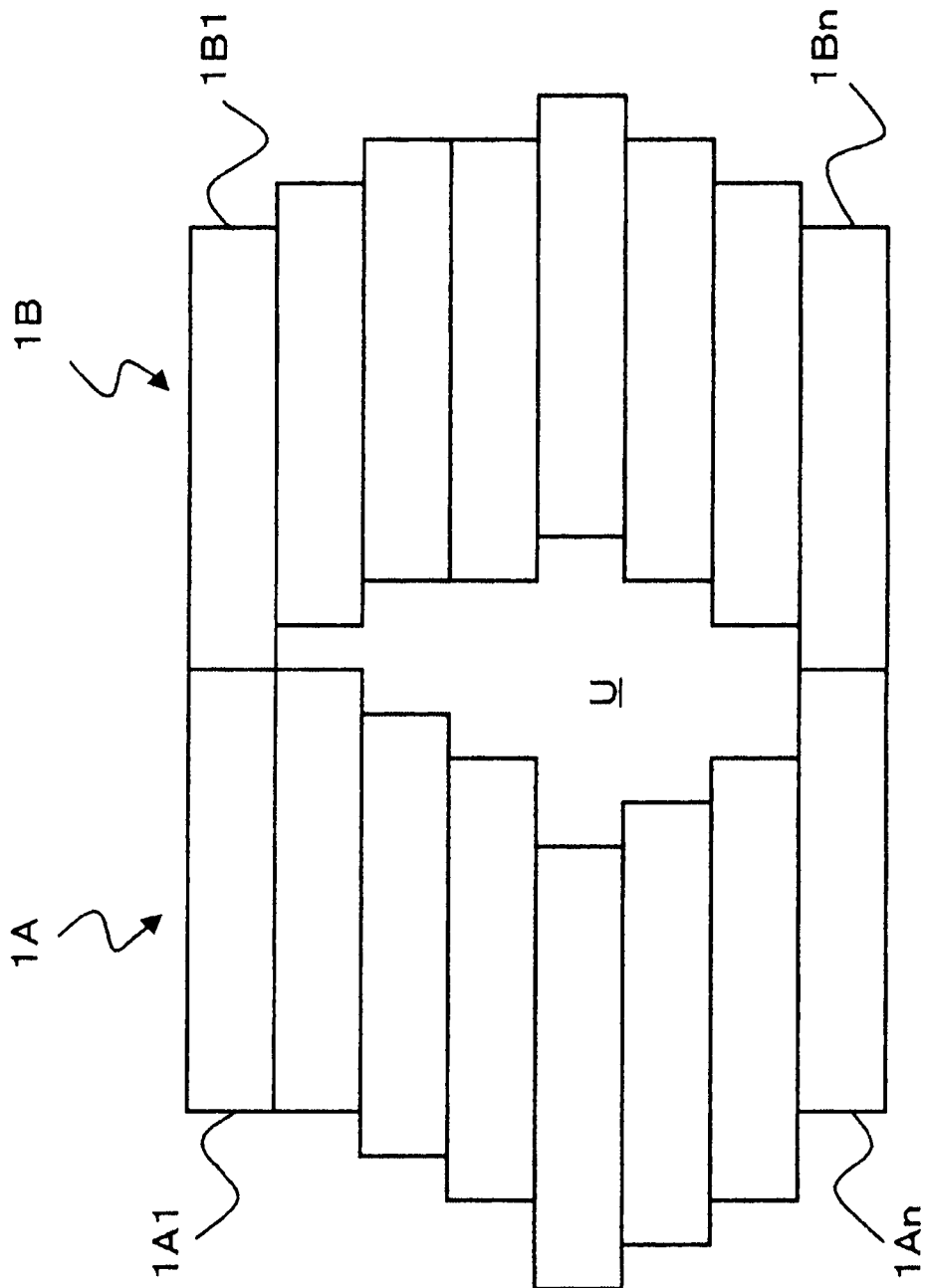
FIG. 8 is a top view which shows the arrangement and the formation of the irradiation field by arranging the leaves included the second collimator in the related art.

In ordinary arrangements, the second collimator components 141A and 141B are configured in a left-right symmetrical manner. Furthermore, with such ordinary arrangements, the leaves 141A1-141An and the corresponding leaves 141B1-141Bn are arranged at fixed positions such that they face one another without any offset. That is to say, with ordinary second collimator, the leaves 141A1-141An and the corresponding leaves 141B1-141Bn are arranged at fixed positions such that they face one another without any offset, as described with reference to FIG. 8.

Figure 7:
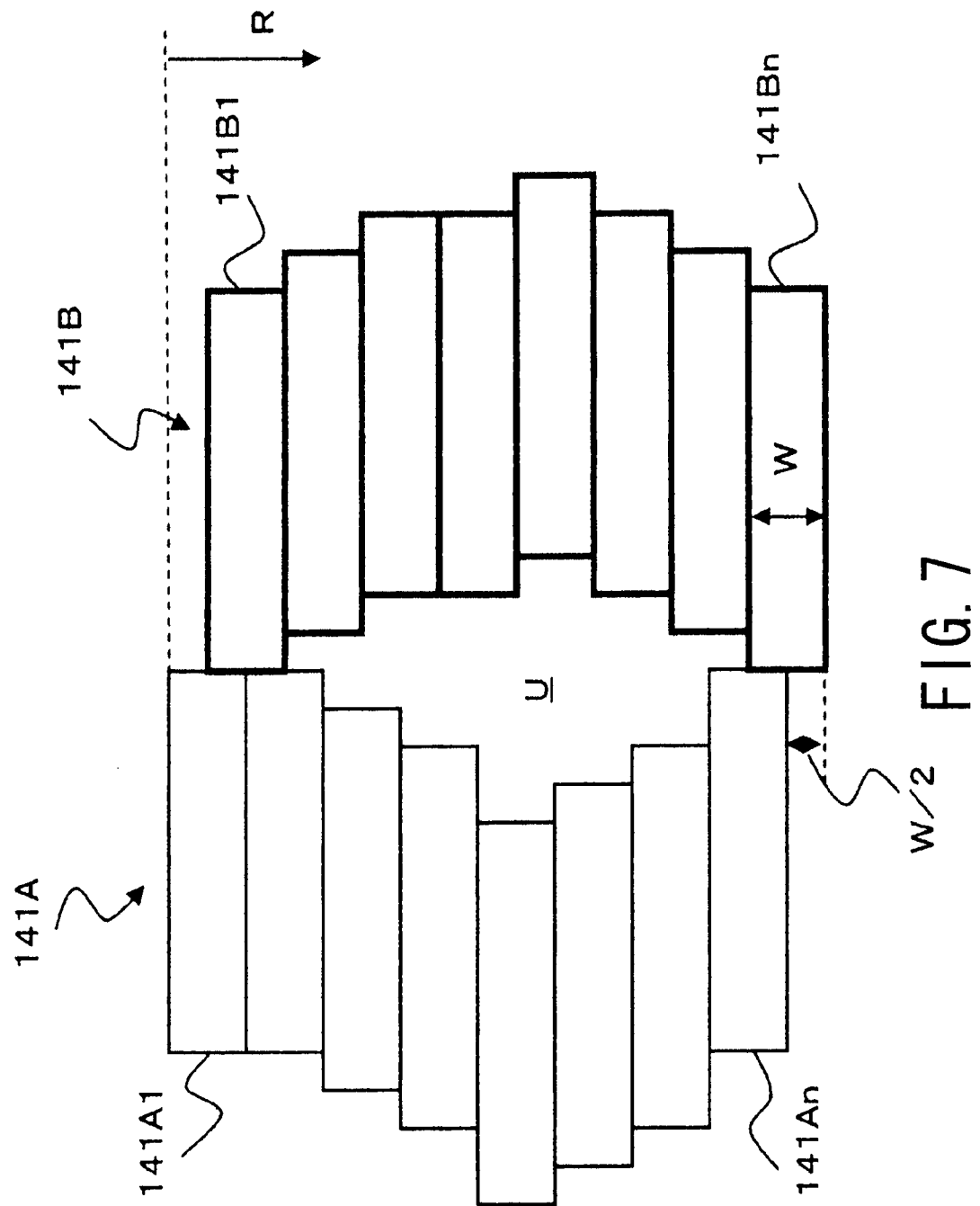
FIG. 7 is a top view which shows an arrangement example and a formation of the irradiation field by arranging the leaves included the second collimator in the present embodiment.

On the other hand, the present invention according to the present embodiment provides an arrangement in which the collimator component 141A having the leaves 141A1-141An and the collimator component 141B having the leaves 141B1-141Bn are arranged at fixed positions such that the end faces of the leaves 141A1-141An and the end faces of the leaves 141B1-141Bn face one another with an offset which is a predetermined value within the range of a leaf-width "W", as shown in FIG. 7. FIG. 7 is an enlarged view of the leaf portion shown in FIG. 5, and shows an arrangement in which the collimator component 141B, which is one component of the second collimator, and the collimator component 141A, which is the other component of the second collimator, are arranged with an offset in the same direction of half the leaf-width "W".

In FIG. 7, the leaves 141B1-141Bn of the one collimator component 141B are indicated by bold lines for convenience of understanding. With such an arrangement shown in FIG. 7, the leaves 141B1-141Bn and the leaves 141A1-141An the opposite collimator component 141A are arranged such that the end faces thereof face each other with an offset of "W/2". FIG. 7 shows an arrangement in which the collimator component 141B is arranged with such an offset by shifting the collimator component 141B toward the leaf 141An, as indicated by an arrow "R". Also, an arrangement may be made in which the collimator component 141B is arranged with an offset by shifting the collimator component 141B toward the leaf 141A1, i.e., in the direction opposite to that indicated by the arrow "R".

Such an arrangement allows the shape of the irradiation field "U" to be adjusted with a minute resolution that corresponds to half the leaf-width "W". However, an arrangement in which the one collimator component 141B is arranged with an offset with respect to the other collimator component 141A in a simple manner changes a part of the area that shields the exposure to radiation into an area through which the therapy part is exposed to radiation. Accordingly, the positions of the end faces of the leaves 141B1-141Bn facing the collimator component 141A should be adjusted such that the irradiation field that includes such a new area through which the therapy part is exposed to radiation approximates the desired irradiation field.

Description has been made regarding an arrangement in which all the leaves 141A1-141An of the second collimator component 141A and the leaves 141B1-141Bn of the second collimator component 141B are formed with the same leaf-width "W". However, the leaves 141A1 and 141An (141B1 and 141Bn), which are positioned at the end of the second collimator component 141A (141B), are preferably formed with a larger leaf-width than those of the other leaves positioned on the inner side thereof. The reason is that such an arrangement prevents the formation of a gap at an edge of the irradiation field "U" provided by an arrangement in which at least one of the second collimator components 141A and 141B is arranged with an offset with respect to the other.

The present invention is not restricted to the above-described embodiment, rather, various embodiments may be made. For example, the range of the offset between the one collimator and the other collimator can be set to a desired value within the range of the leaf-width "W".

Also, an arrangement may be made including a mechanism which adjusts the offset between the one collimator component 141B and the other collimator component 141A within the range of the leaf-width "W", instead of an arrangement in which the one collimator and the other collimator are arranged with a fixed offset in the leaf-width direction. Such an arrangement provides a minute adjustment of the irradiation field "U", thereby providing the irradiation field "U" approximating the desired shape with high resolution. That is to say, in order to adjust the irradiation field "U" described with reference to FIG. 2 and FIG. 3, such an arrangement has a function of adjusting at least one of the positions of the second collimator components 141A and 141B to a certain extent in the orthogonal direction to the moving direction in which the distances between the leaves 141A1-141An and 141B1-141Bn are adjusted (i.e., the X direction in which the distance between the first collimator components 140A and 140B is adjusted).

In order to adjust the positions of the second collimator components 141A and 141B in such a manner, such an arrangement employs a similar mechanism to that for the first collimator components 140A and 140B, which allows at least one of the second collimator components 141A and 141B to be moved in the direction of the arrow "X" along the arc-shaped path around the radiation source "S" as the center. Alternatively, an arrangement may be made in which a lead screw provided to each second collimator component is driven by a motor. With such an arrangement, the movement of the second collimator component is detected by an encoder, a potentiometer, or the like, thereby allowing the position of the second collimator component to be detected and adjusted in a simple manner. It should be noted that, when both the second collimator components 141A and 141B are moved along the direction of the arrow "X", the second collimator components 141A and 141b are moved in directions opposite to one another (i.e., the direction of the arrow "R" shown in FIG. 7 and the direction opposite thereto). Furthermore, with such an arrangement, the second collimator components 141A and 141B, which face one another, are moved along the arc-shaped path around the radiation source "S" as the center. This eliminates the problem of a penumbra in the irradiation field "U".

As described above in detail, without employing a multi-leaf collimator having a two-stage configuration, the present embodiment provides the irradiation field "U" with approximately the same minute resolution as that provided by an arrangement employing the multi-leaf collimator having a single-stage configuration including an increased number of leaves. That is to say, such an arrangement allows the irradiation field "U" to be formed in a simple manner such that it approximates, with higher precision, the shape of the therapy part, which can develop in various shapes. With such an arrangement, the irradiation field "U" thus formed is exposed to radiation. This allows only the site of the disease, which is to be treated, to be irradiated while protecting the healthy tissue from being exposed to radiation.

Also, an arrangement may be made having an additional function of adjusting, with the minute resolution, at least the positions of the second collimator components 141A and 141B. Such an arrangement allows the shape of the irradiation field "U" to be adjusted such that it approximates a desired shape with higher precision. Thus, such an arrangement protects the object from unnecessary exposure to radiation, thereby improving the safety of the therapy. Furthermore, such an arrangement does not involve a large-size multi-leaf collimator device, thereby eliminating the problem of occupying a large part of a space for the therapy. Thus, the present invention provides an extremely useful radiation therapy apparatus.

What is claimed is:

1. A radiation therapy apparatus comprising:

a multi-leaf collimator device including a pair of collimator components on a same plane, each collimator component including a plurality of leaves, one collimator component of the pair of collimator components and an other collimator component of the pair being arranged close to one another such that the collimator components face one another across an irradiation axis and set a desired irradiation field by individually moving the leaves, wherein leaves of the one collimator component are arranged with an offset with respect to leaves of the other collimator component along a direction in which the leaves of the one collimator component are arranged, within a range of a leaf-width.

2. A radiation therapy apparatus according to claim 1, wherein the leaves are movable individually along an arc-shaped path around a radiation source as a center.

3. A radiation therapy apparatus according to claim 2, wherein the leaves are arranged orthogonally to a moving direction of the leaves along the arc-shaped path.

4. A radiation therapy apparatus according to claim 1, wherein the offset with which the collimator components are arranged is approximately half the leaf-width.

5. A radiation therapy apparatus, comprising:
a multi-leaf collimator device including a pair of collimator components on a same plane, each collimator component including a plurality of leaves, one collimator component of the pair of collimator components and an other collimator component of the pair being arranged close to one another such that the collimator components face one another across an irradiation axis and set a desired irradiation field by individually moving the leaves,
wherein the one collimator component is movable with respect to the other collimator component along a direction in which the leaves of the one collimator component are arranged.

6. A radiation therapy apparatus according to claim 5, wherein the leaves are movable individually along an arc-shaped path around a radiation source as a center.

7. A radiation therapy apparatus according to claim 6, wherein the leaves are movable and arranged orthogonally to a moving direction of the leaves along the arc-shaped path.

8. A radiation therapy apparatus according to claim 5, wherein at least one of the collimator components is movable in a range of approximately half the leaf-width.

* * * * *